Figure 1:
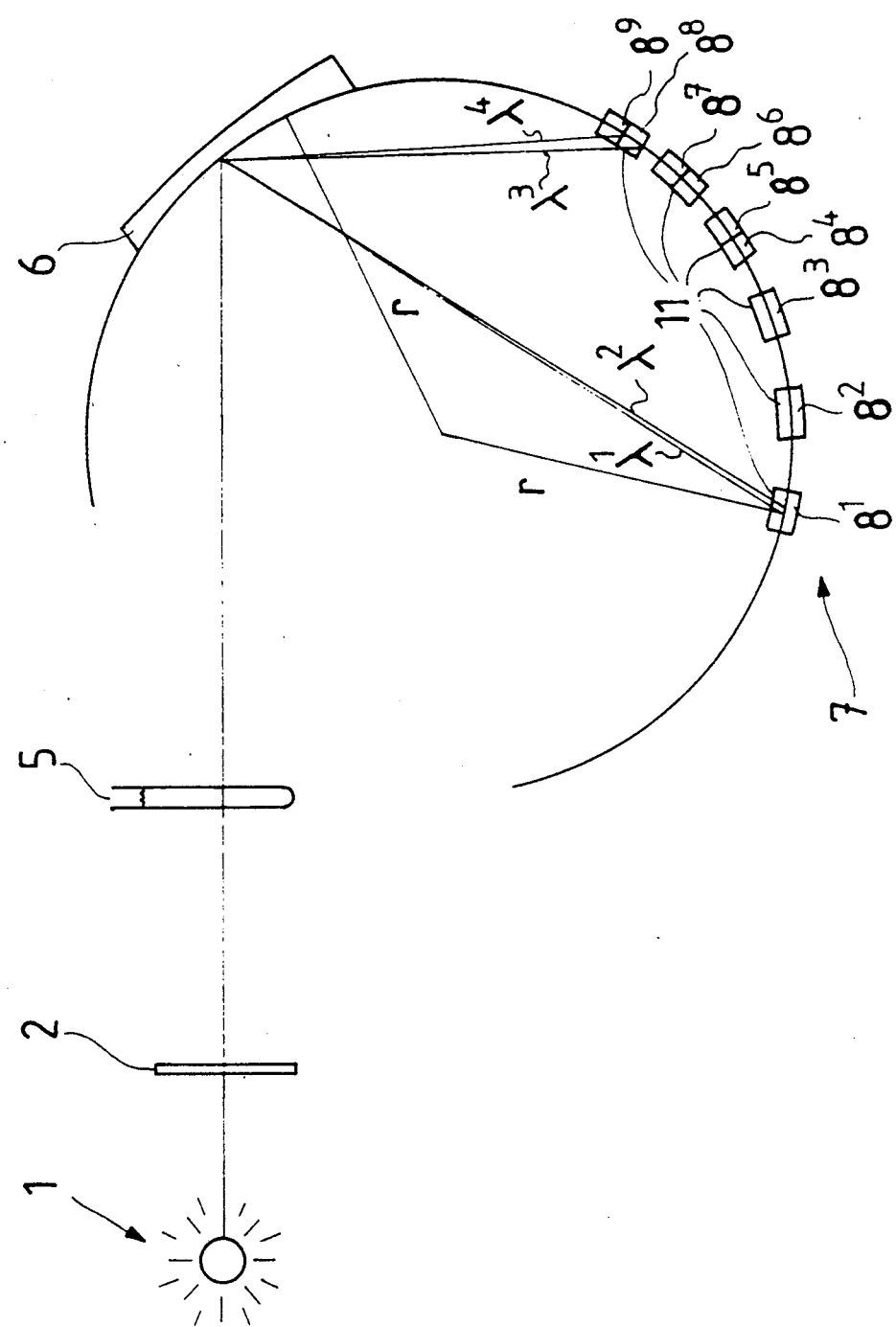

United States Patent [19]

Räsänen

[11] Patent Number: 5,017,785

[45] Date of Patent: May 21, 1991

[54] IR-SPECTROMETRIC ANALYZING PROCEDURE AND MEANS

[75] Inventor: Jaakko Räsänen, Espoo, Finland

[73] Assignee: Oy Dailab Inc., Espoo, Finland

[21] Appl. No.: 447,188

[22] Filed: Dec. 7, 1989

[30] Foreign Application Priority Data

Feb. 16, 1989 [FI] Finland .................................. 890758

[51] Int. Cl.$^5$ ............................................. G01J 3/427
[52] U.S. Cl. .................................... 250/345; 250/339;
250/343; 356/51; 356/328
[58] Field of Search ............... 356/320, 328, 326, 319,
356/51; 250/343, 339, 345, 346

[56] References Cited

U.S. PATENT DOCUMENTS

| | | | |
|---|---|---|---|
| 3,174,037 | 3/1965 | Demorest et al. | 250/343 |
| 4,030,828 | 6/1977 | Sonobe et al. | 356/320 |
| 4,214,835 | 7/1980 | Roos | 356/328 |
| 4,279,511 | 7/1981 | Maute et al. | 356/328 |
| 4,557,601 | 12/1985 | Kuroishi et al. | 356/320 |
| 4,571,074 | 2/1986 | Thevenon | 356/51 |
| 4,781,456 | 11/1988 | Nogami | 356/320 |
| 4,841,140 | 6/1989 | Sullivan et al. | 356/328 |

FOREIGN PATENT DOCUMENTS 159289 12/1979 Japan .................................. 356/320

Primary Examiner—Carolyn E. Fields
Attorney, Agent, or Firm—Merchant & Gould

[57] ABSTRACT

An IR-spectrometric analyzing procedure, the measuring absorbance and reference absorbance being detected simultaneously from an IR light beam conducted to pass through the sample and diffracted to a spectrum. An IR spectrometer comprising a light source (1), a sample cuvette (5), a diffraction member (6), detectors (7) and a calculating means (9) for determining the content values of the sample corresponding to the measuring absorbance, the detectors (7) having been arranged to detect the measuring absorbance and the reference absorbance simultaneously from the beam that has passed through the sample and been diffracted to a spectrum.

14 Claims, 2 Drawing Sheets

IR-SPECTROMETRIC ANALYZING PROCEDURE AND MEANS

The present invention concerns an IR-spectrometric analysing procedure, as has been defined in the preamble to claim 1.

The invention further concerns an IR spectrometer, as has been defined in the preamble to claim 10.

IR spectrometers are commonly employed in a great variety of chemical analyses. In IR spectrometers is formed an IR absorption spectrum characterizing the substance that is being analysed and the contents of components therein. The spectrum is produced from the radiation intensity as a function of wavelength. When the spectrum is analysed, a comparison is made of its peak regions, the absorption maxima, and the corresponding absorbance value of a reference sample.

It is known in the art to determine contents of substances causing absorption in the IR range by a procedure wherein first is measured the absorbance at the wavelength corresponding to a chemical bond typical of the substance in question, at which said bond has an absorption maximum, and thereafter is measured a reference absorbance at another wavelength differing from the absorption maximum. The content of the substance is calculated by comparing the two absorbances.

For instance to the purpose of measuring the fat, protein and lactose present in milk and milk products with IR light, it is common practice to use a rotating filter disk on which are mounted filters corresponding to the measuring absorbance and reference absorbance of each substance to be measured. In the measurements corresponding filters are used, and the filters are changed as required.

When measurements are performed, the optical point of measurement is located in a measuring cuvette, whereby between measurements movements of molecules of the constituents from one location to another can take place even while the solution or suspension to be measured is merely standing in the cuvette. As a result, conditions in the measuring cuvette at two consecutive points of time may differ even greatly.

This means in practice that a reference absorbance measurement and a sample absorbance measurement made at different times cannot usually be made of the same molecules nor under the same conditions of measurement. Therefore a measuring system based on different measuring times cannot operate as a reliable arrangement which would be able to yield correct content values.

Content readings of different substances measured on one and the same sample may also be unreliable because they too are measured at different times, and possibly under different conditions in the measuring cuvette. The situation becomes particularly problematic when the sample that is being measured is a dispersed system, for instance an emulsion or a suspension, of which the dispersed constituents turbulate in the measuring cuvette. This situation obtains, for instance, in the case of milk and of products processed from milk, both containing for instance fat globules and casein, which is either solid or semi-solid, depending on its degree of polymerization.

As a rule, the parameters of the IR spectrometer, the analysing conditions and/or the quality of the samples change continuously so that one has to perform frequent calibration runs, up to several per day. In particular, the filters of the IR spectrometer are sensitive to temperature variations, and thus temperature variations cause inaccuracy in the end results. Furthermore, the way in which the grating or equivalent, the light source, detector, sample cuvette or equivalent component or member is mounted may cause displacement of said component e.g. as a consequence of temperature variation, vibration or the like.

Moreover, the components of IR spectrometers of prior art, e.g. IR filters, are rather expensive, and this fact substantially increases the price of IR spectrometers.

The object of the present invention is to eliminate the drawbacks pointed out in the foregoing and to provide a novel IR-spectrometric analysing procedure and means in which the drawbacks presented above do not occur to such extent as heretofore.

It is particularly an aim of the invention to provide a novel IR-spectrometric analysing procedure and means which are particularly well suited for determining the contents of the components of various emulsions and suspensions, in particular of mixtures encountered in the foodstuff industry.

It is particularly an aim of the invention to provide a novel IR-spectrometric analysing procedure and means in which the characteristic quantities, particularly the position of light source, grating or equivalent, detector, sample cuvette or other components or members will not change as easily as they do in earlier IR spectrometers.

Regarding the features characterizing the invention, reference is made to the claims.

The invention is based on the fundamental idea that the detector has been arranged to detect the measuring absorbance and the reference absorbance simultaneously from a light beam that has passed through the sample and has been diffracted to a spectrum. This may for instance be implemented in that the light radiating from an IR source is directed on the sample placed in a sample cuvette, the light obtained from the cuvette is diffracted, or divided, to produce a spectrum, by optical means with the aid of a diffraction member, e.g. a curved grating or a prism. From the spectrum thus obtained the measuring absorbance and reference absorbance corresponding to given desired wavelengths, or their difference, are detected with the aid of a detector or detectors, i.e., in the measuring absorbance and reference absorbance detector, or detectors, are formed signals corresponding to the measuring absorbance and to the reference absorbance or to their ratio or difference or another quantity dependent on them.

The wavelengths corresponding to the detected measuring absorbance and reference absorbance are naturally determined in accordance with the point of measurement in the IR spectrum. The points of measurement may for instance be selected to correspond to the absorbance peaks of desired components, or to correspond to desired absorbance values. The measuring absorbance and reference absorbance are then advantageously determined in two mutually adjacent wavelength intervals of the IR spectrum. The measuring absorbance is advantageously detected at a peak of the IR spectrum and the reference absorbance, at the minimum immediately beside the peak.

Calculations are based on using an internal reference, that is, the reference value is determined from the sample, e.g. the IR spectrum in accordance with an absorbance value which is constant at different concentrations of the respective component. The content of the measured component can then be calculated directly on the basis of the ratios of the detected measuring absorbance and reference absorbance, or similarly on the basis of their difference.

Determination of a given desired component is made by calculation in a way known in itself in the art; the implementation of the calculations, and calculating means, for finding the content of a given component are known in themselves and shall not be described in greater detail in this connection.

With the procedure and means of the invention excellent reliability of the measurements is achieved. The measuring absorbance and reference absorbance are detected at the same moment and under identical conditions, that is from the same molecules. The result is highly reliable and represents the sample such as it was at the time of measurement, at the point of measurement, and without any potential changes taking place as a function of time.

The procedure and means of the invention are applicable in IR-spectrometric measurements exceedingly well in the case of dispersed systems, e.g. emulsions and suspensions, in which the measuring errors occurring due to the effect of turbulence are eliminated, thanks to the invention. One may thus particularly contemplate emulsions selected from the group: fat-, protein emulsions, and possibly in addition a substance selected from the group: carbohydrates, urea and other ketone substances, and antibiotics.

Another important advantage gainable with the invention is the swiftness of the measurements, that is, that the measuring absorbance and the reference absorbance, or their difference or equivalent signals, can be detected simultaneously in a very brief moment, which is on the order of milliseconds in practice. Being such, the arrangement is remarkably faster than e.g. the use of a filter disk known through the state of art, in the case of which each measurement requires two consecutive measuring operations. When the absorbance values of several substances are measured from one sample and two absorbance readings are taken for each substance, the measuring process takes long and is unreliable using a filter disk.

Furthermore with the invention the major advantage is gained that it is not necessary to use in the device any filters likely to undergo ageing, and presenting performance values which change with time.

Furthermore, when a grating is used for diffraction member, no moving parts subject to wear are required in the optics, whereby the characteristic properties of the means will be unchanged and results of measurement are mutually comparable.

A diffraction member is here understood to be any kind of member diffracting an IR beam to a spectrum, such as a grating, prism or other member in which IR radiation produces a spectrum.

The diffraction member is advantageously curved and constitutes part of a circle, cylinder or spherical surface.

The detector or detectors are advantageously placed substantially ob the periphery of the sane circle, or on the surface of the same sphere, as the diffraction member.

The means comprises one, advantageously several, detectors which detect the intensity of the IR spectrum incident on the location of the detector, at the respective point. The system that is used may consist of one or several detectors. If two separate detectors are used, one may be disposed to detect the measuring absorbance and the other the reference absorbance. The detector may further be for instance a dual beam detector which measures differential intensities between IR beams entering the detector, such as e.g. a pyroelectric dual beam detector, manufactured e.g. by Hamamatsu, Japan, or by Eltec, U.S.A., etc.

The light source, diffraction member and detector or detectors are advantageously fixedly mounted in relation to each other.

Figure 2:
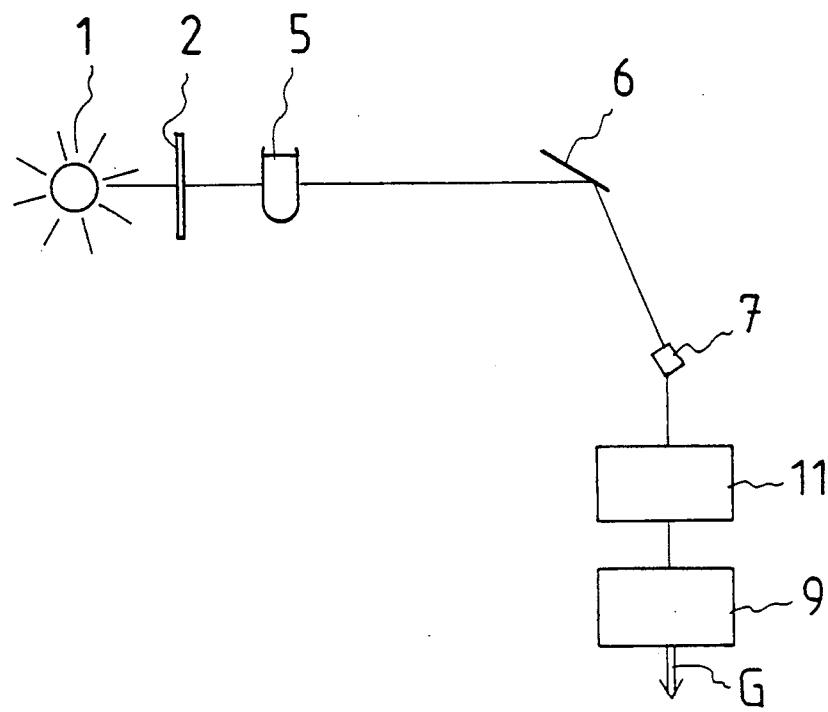
Figure 3:
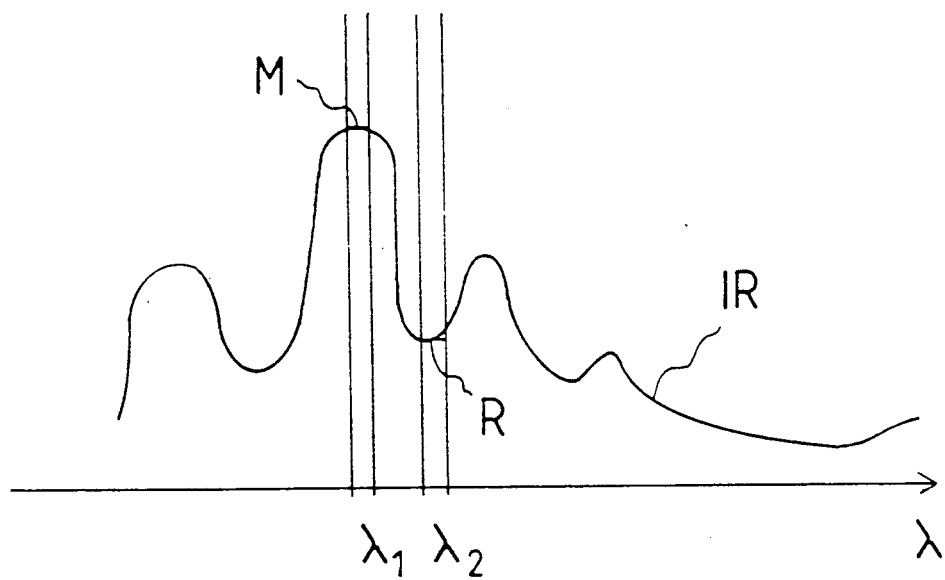

The invention is described in the following in detail with the aid of an embodiment example, referring to the attached drawing, wherein:

FIG. 1 presents schematically an IR spectrometer according to the invention;

FIG. 2 presents a schematic diagram showing the implementation of the procedure of the invention; and FIG. 3 presents the measuring absorbance and reference absorbance bands in a measurement according to the invention.

In FIG. 1 is seen an IR spectrometer according to the invention. The spectrometer substantially comprises the following elements known in themselves in the art: a light source 1, a chopper 2, a sample cuvette 5, a diffraction member 6 and a detector 7. The light rays are directed through the sample cuvette 5 into the diffraction member 6.

The chopper 2 is of any previously known kind whatsoever, for instance a mechanical chopper with a rotating punched plate through which the light beam is conducted. The chopper is previously known through IR spectrometers and is not more closely described in this connection. A chopper is usually necessary because as a rule IR detectors measure IR radiation intensities on the basis of the respective changes.

The diffraction member in the well-known way disperses the light beam into a spectrum, which is detected with the aid of the detector 7. The diffraction member 6, such as a grating, prism or other diffraction member dispersing light to produce a spectrum, is advantageously curved. The side of the diffraction member facing the light beam substantially forms part of a circular surface. The diffraction member may constitute, for instance, part of a spherical surface, it may be a planar part of a cylindrical surface, or it may constitute part of a circular arc.

The diffraction member is advantageously disposed on a circular arc or on the surface of a sphere. The detector 7 is then advantageously disposed on the same circular arc or on the surface of the same sphere.

The means advantageously comprises at least one dual detector; in the embodiment presented there have been depicted three separate dual detectors $8^1$–$8^3$, each one of them measuring the intensity of the corresponding location in the IR spectrum arriving at the respective site, at two different points; e.g. pyroelectric IR detectors. The detectors have been disposed to measure intensities of the light beam conducted from the light source through the sample, at different points of the spectrum, that is, to produce the corresponding signals or a quantity dependent thereon, such as their quotient or difference.

The means depicted in FIG. 1 further comprises three pairs of detectors $8^4$, $8^5$; $8^6$, $8^7$ and $8^8$, $8^9$, which have been disposed to measure two different IR wavelengths, a measuring absorbance and a reference absorbance each pair.

The detectors have been placed at desired points on the circumference. The dimensions of the circle, cylinder or sphere defined by light source, chopper, cuvette and diffraction member can be arranged for instance so that 1 mm on said circumference corresponds to a wavelength differential of e.g. 100 nm, or to another given wavelength differential. Furthermore the detectors, for instance two mutually adjacent detectors, may be arranged so that the spacing of the points of measurement of the dual detector, respectively the spacing of the two separate detectors, is 1 mm and they have been placed so that one point of measurement, respectively one detector, coincides in location with an absorbance maximum of the IR spectrum and the other point of measurement, respectively detector, is located at the preceding, adjacent minimum to measure the background, that is, the substantially constant reference level.

When an IR spectrum is being measured with the means of the invention, the IR spectrum is formed in a manner known in itself in the art, by effect of the diffraction member, on the inner surface of the respective sphere. Those dual beams, that is absorbances, which are desired are detected, that is measured as such, their ratio is measured, the differential voltage produced by them is measured or the ratio dependent on them is measured, whence the respective content can be determined directly with the aid of a signal processing unit 11 and a calculating means 8, e.g. a computer, and with the aid of the known reference absorbance of the sample.

In FIG. 1, the light source 1, chopper 2, sample cuvette 5, diffraction member 6 and detectors 7 have been advantageously mounted fixedly in relation to each other. Then, the characteristic properties of the IR spectrometer will not change significantly during analysis, and there is no need to move or turn the diffraction member or the detectors relative to each other.

In FIG. 1 the dual detector 8' has been arranged to measure the difference between the measuring absorbance $\lambda_1$ and reference absorbance $\lambda_2$ of the beam that has been conducted through the sample 5 to the diffraction member 6 and dispersed to a spectrum to constitute a measuring beam and a reference beam.

Further in FIG. 1 the detector pair $8^8$, $8^9$ has been arranged to measure the measuring absorbance $\lambda_3$ and reference absorbance $\lambda_4$ of the beam dispersed by the diffraction member 6 to a spectrum.

In FIG. 2 is seen the implementation of the procedure of the invention, mainly employing an arrangement as shown in FIG. 1. The light beam formed by the light source 1 is carried to the chopper 2 and further through the sample cuvette 5 to the diffraction member 6. The diffraction member disperses the light to a spectrum, and the desired part of the spectrum is measured with the aid of two detectors, e.g. $8^8$, $8^9$ (FIG. 1). The detectors $8^8$, $8^9$ detect the wavelength region of a given maximum of the IR absorption spectrum, that is the measuring interval M, $\lambda_4$ and simultaneously the reference point R of the minimum adjacent to said maximum, that is the wavelength interval $\lambda_2$. The IR spectrum IR, measuring interval M and reference interval R have been illustrated in FIG. 3. The detectors produce signals corresponding to the measured absorbances, the measuring absorbance M and the reference absorbance R, which have been conducted to an amplifier/signal processing unit 11, which processes the signals. Finally, the results of measurement obtained from the signal processing unit have been carried to a calculating means 9, such as a microprocessor, for producing the measurement-of-content result C of the desired component.

When dual beam detectors are used, such as pyroelectric dual beam detectors, these are exceedingly low in price. Furthermore, no specific, expensive filter is required in the detector, whereas conventional equivalent apparatus usually contains a filter for the particular desired wavelength. Furthermore, thanks to the pyroelectric dual beam detectors, which are internally connected to oppose each other and are therefore compensated in view of temperature and vibration, the output voltage will be smooth, corresponding to the differential intensity measured, that is e.g. to the concentration of the measured solution.

The embodiment example is merely meant to illustrate the invention, and any embodiments of the invention may vary within the scope of the claims following below.

What is claimed is:

1. An IR-spectrometric analyzing procedure for analyzing the components of a dispersed system subject to turbulence affecting the spectrometric analysis, wherein an IR light beam is produced; the IR light beam is conducted through a single sample cuvette containing the sample; the IR light beam thus obtained is diffracted to a spectrum; the measuring the absorbance and reference absorbance are detected at a plurality of pairs of predetermined, fixed, adjacent points in the spectrum by dual beam detectors and a quantitative analysis value is determined from the ratio of the difference between the pairs of detected measuring and reference absorbances, characterized in that the pairs of measuring absorbance and reference absorbance are detected simultaneously from the IR light beam conducted through the single sample and diffracted to a spectrum and detected at predetermined pairs of fixed points by dual beam detectors.

2. Procedure according to claim 1, characterized in that the IR beam is conducted from the single sample to a diffraction member placed substantially on the periphery of a circle and the measuring absorbance and reference absorbance are detected at a plurality of peripheral adjacent points of the same circle.

3. Procedure according to claim 1, characterized in that each measuring absorbance and reference absorbance pair is detected in two mutually adjacent wavelength intervals of he IR spectrum.

4. Procedure according to claim 3, characterized in that each measuring absorbance is detected at a peak of the IR spectrum, and each reference absorbance at a minimum immediately adjacent to said peak.

5. Procedure according to claim 4, characterized in that the difference of the measuring and reference absorbances is formed in each dual beam detector.

6. Procedure according to claim 4, characterized in that the dispersed system to be measured is an emulsion selected from the group consisting of fat and protein emulsions.

7. Procedure according to claim 6, characterized in that the dispersed system contains a substance selected from the group consisting of carbohydrates, urea and other ketone substances, and antibiotics.

8. An IR spectrometer for analyzing the components of a dispersed system subject to turbulence affecting the spectrometric analysis comprising an IR light source (1) for forming a light beam; a single sample cuvette (5) which has been placed in the path of said beam; a diffraction member (6) for diffracting to a spectrum the light beam that has passed through the sample; a plurality of dual beam detectors (7) for detecting measuring absorbances at desired adjacent points in the spectrum and for detecting the reference absorbances at corresponding points of the spectrum, and a calculation means (9) for determining the content value of the sample corresponding to the measuring absorbances, on the basis of the ratio between the detected measuring and reference absorbances, characterized in that the dual beam detectors (7) have been arranged to detect the pairs of measuring absorbances and reference absorbances simultaneously from the light beam that has passed through the sample and has been diffracted to a spectrum.

9. The IR spectrometer according to claim 8, characterized in that the diffraction member (6) has been placed substantially on a circular arc (10) and the detectors (6) have been placed substantially on an arc of the same circle.

10. The IR spectrometer according to claim 8, characterized in that the dual beam detectors (6) have been arranged to detect the measuring absorbance and the reference absorbance in two mutually adjacent wavelength intervals of the IR spectrum.

11. The IR spectrometer according to claim 10, characterized in that the detectors (6) have been arranged to detect the measuring absorbance at a peak in the IR spectrum and the reference absorbance, at a minimum immediately adjacent to said peak.

12. The IR spectrometer according to claim 11, characterized in that the light source (1), the diffraction member (6) and the detectors (7) are mounted substantially fixedly in relation to each other.

13. The IR spectrometer according to claim 12, characterized in that the detectors (6) are separate.

14. The IR spectrometer according to claim 10, characterized in that each dual beam detector ($8^1$) comprises means for forming the difference of the measuring absorbance and the reference absorbance.

* * * * *